United States Patent [19]
Wimalawansa

[11] Patent Number: 5,958,877
[45] Date of Patent: Sep. 28, 1999

[54] METHOD FOR COUNTERACTING VASOSPASMS, ISCHEMIA, RENAL FAILURE, AND TREATING MALE IMPOTENCE USING CALCITONIN GENE RELATED PEPTIDE

[76] Inventor: Sunil J. Wimalawansa, 907 Laurel Field, Friendswood, Tex. 77546

[21] Appl. No.: 08/446,929

[22] Filed: May 18, 1995

[51] Int. Cl.$^6$ .......................... A61K 38/22; A61K 38/23
[52] U.S. Cl. ................................ 514/12; 514/21; 514/929
[58] Field of Search .................................. 530/307, 324; 514/12, 21, 929

[56] References Cited

U.S. PATENT DOCUMENTS

| | | | |
|---|---|---|---|
| 5,214,030 | 5/1993 | Stief | 514/11 |
| 5,290,799 | 3/1994 | Misra et al. | 514/365 |
| 5,318,531 | 6/1994 | Leone | 604/96 |
| 5,342,348 | 8/1994 | Kaplan | 604/891.1 |
| 5,399,352 | 3/1995 | Hanson | 424/423 |
| 5,550,110 | 8/1996 | Cody et al. | 514/17 |
| 5,571,523 | 11/1996 | Lee et al. | 424/423 |
| 5,576,290 | 11/1996 | Hadley et al. | 514/11 |
| 5,637,309 | 6/1997 | Tajima et al. | 424/423 |

OTHER PUBLICATIONS

Jean McEwan, M.D., CH. B., "Calcitonin gene–related peptide: a potent dilator of human epicardial coronary arteries," *Circulation*, 74:6 (Dec. 1986) 1243–1247.

Peter F. Ludman, et al, "Effects of Calcitonin Gene–Related Peptide on Normal and Atheromatous Vessels and on resistance Vessels in the Coronary Circulation in Humans," *Circulation*, 84:5 (Nov. 1991) 1993–2000.

J.R. McEwan, M.B.CH.B., et al., "Vasodilation by calcitonin gene–related peptide and by substance P: a comparison of their effects on resistance and capacitance vessels of human forearms," *Circulation*, 77:5 (May 1988) 1072–1080.

Nobuyo Sekiguchi, MD, et al, "Effect of Calcitonin Gene–Related Peptide on Coronary Microvessels and Its Role in Acute Myocardial Ischemia," *Circulation*, 89:1, (Jan. 1994).

Sunil J. Wimalawansa, et al, "Isolation, Purification and Characterization of B–hCFRP From human Spinal Cord," *Biochemical and Biophysical Research Communications*, 167:3 (Mar. 1990) 993–1000.

Donald J. DiPette, et al. "Cardiovascular Actions of Calcitonin Gene–Related Peptide," *Calcium Regulating Hormones and Cardiovascular Function*, (Jun. 1995) 239–252.

Neal F. Uren, et al. "Effect of intravenous calcitonin gene related peptide of ischaemia threshold and coronary stenosis severity in humans," *Cardiovascular Research*, 27 (1993) 1477–1481.

David Ezra, et al., "Calcitonin gene–related peptide: a potent modulator of coronary flow," *European Journal of Pharmacology*, 137 (1987) 101–105.

Jacek, J. Preibisz, "Calcitonin Gene–Related Peptide and Regulation of Human Cardiovascular Homeostasis," *American Journal of Hypertension, Ltd.*, 6:5 (May 1993) 435–450.

T. Shoji, et al. "Vasodilating effects of human and rat calcitonin gene–related peptides in isolated porcine coronary arteries," *Naunyn–Schmiedeberg's Arch Pharmacol*, 336 (Jul. 1987) 438–444.

(List continued on next page.)

*Primary Examiner*—Jeffrey E. Russel
*Attorney, Agent, or Firm*—Rosenblatt & Redano P.C.

[57] ABSTRACT

The present invention provides a method for counteracting vasospasms and treating male impotence using calcitonin gene-related peptide (CGRP). CGRP is a naturally occurring substance in the human body. As such, CGRP does not have the same toxicity and allergy problems as the foreign substances that currently are used for similar purposes. When locally applied or infused, the effects of CGRP are limited to a local vascular area. Virtually no systemic effects are induced, making CGRP extremely safe and effective.

28 Claims, 1 Drawing Sheet

OTHER PUBLICATIONS

Brian B. Quebbemen, et al, "Effect of Calcitonin Gene–Related Peptide on Well–Developed Canine Coronary Collateral Vasculature," *Journal of Cardiovascular Pharmacology,* 21:5 (1993) 774–780.

Sunil J. Wimalawansa, "Calcitonin: Molecular Biology, Physiology, Pathophysicology and its Theraputic Uses," 121–160, (not dated).

Michael G. Rosenfeld, et al. "Production of a novel neuropeptide encoded by the calcitonin gene via tissue–specific RNA processing," *Nature,* 304 (Jul. 1983) 129–135.

Sunil J. Wimalawansa, "Use of Synthetic Peptides in Specific Affinity Chromatography for Purification of Specific Peptide Receptors" *Inovation and Perspectives in Solid Phase Synthesis; (Peptides, Polypeptides and Oligonucleotides),* (1992) 111–119.

Sunil J. Wimalawansa, "Isolation, Purification, and Biochemical Characterization of Calcitonin Gene–Related Peptide Receptors," *Annals of the New York Academy of Science,* 657 (1992) 70–87.

Howard R. Morris, et al. "Isolation and characterization of human calcitonin gene–related peptide," *Nature,* 308 (Apr. 1984) 746–748.

J.W.M. Hoppener, et al. "The second human calcitonin/CGRP gene is located on chromosome 11." *Human Genetics,* 70 (1985) 259–263.

P.H. Steenbergh, et al. "A second human calcitonin/CGRP gene," *FEBS Letters,* 183:2 (Apr. 1985) 403–407.

METHOD FOR COUNTERACTING VASOSPASMS, ISCHEMIA, RENAL FAILURE, AND TREATING MALE IMPOTENCE USING CALCITONIN GENE RELATED PEPTIDE

FIELD OF THE INVENTION

The present invention relates to the local administration of calcitonin gene-related peptide (CGRP) to treat male impotence, and to prevent vasospasms induced by vasoconstrictor peptides, particularly during angioplasty or to prevent reocclusion of blood vessels during and/or after either angioplasty, stent insertion, or the implantation of a vascular graft.

BACKGROUND OF THE INVENTION

A number of vasoconstrictor peptides produced by the body induce vasospasms, particularly when blood supply to a region is reduced for some reason. Vasospasms are common when a patient is afflicted with an obstructed artery, such as the coronary artery, and during ischemia associated with many organs, such as the heart, brain, and kidney. Vasospasms are particularly common during and after medical procedures that reduce the blood flow in the vicinity of the procedure. Examples of such procedures are angioplasty and the implantation of vascular grafts. Vasospasms also are a contributing factor to the reocclusion of arteries after angioplasty, stent insertion, or other reconstructive arterial, or trauma surgery.

Angioplasty is a procedure for dilating an obstructed artery. One common type of angioplasty is known as percutaneous transluminal coronary angioplasty ("PTCA"). PTCA is performed using a "balloon" catheter, or a PTCA catheter. A balloon catheter consists, very basically, of an inflatable balloon and a means for guiding the balloon to the target occlusion and for inflating the balloon to dilate the artery at the point of the occlusion. Preferably, the catheter also permits simultaneous monitoring of aortic pressure and/or simultaneous dye injection to clarify the vascular anatomy.

During angioplasty, the blood flow through the target artery is greatly reduced, resulting in angina. As a result, it often is necessary to infuse drugs or oxygenated blood distal to the stenosis in order to maintain adequate physiological function of the target organ. The drugs that are commonly used to dilate the artery are substances that do not naturally occur in the human body. These foreign substances have the potential for toxicity and for inducing an allergic reaction. Since the patient already is in a stressed condition due to the angioplasty procedure, itself, such reactions are undesirable. A more natural method for dilating arteries to counteract vasospasms, which does not create such a risk of toxicity and allergic reaction, would be highly desirable.

Furthermore, approximately 8% of all coronary angioplasty leads to a rapid reocclusion at the site of the procedure. Currently, such reocclusions are treated either by insertion of an intracoronary stent or by emergency coronary artery by-pass surgery. A less invasive method for treating reocclusion of vessels after angioplasty and similar procedures is sorely needed.

SUMMARY OF THE INVENTION

The present invention provides a method for counteracting vasospasms and treating male impotence using calcitonin gene-related peptide (CGRP). CGRP is a naturally occurring vasodilator substance in the human body. As such, CGRP does not have the same toxicity and allergy problems as the foreign substances that currently are used for similar purposes. When locally applied or infused, the effects of CGRP are limited to a local vascular area. Virtually no systemic effects are induced, making CGRP extremely safe and effective.

DETAILED DESCRIPTION OF THE INVENTION

Figure 1:
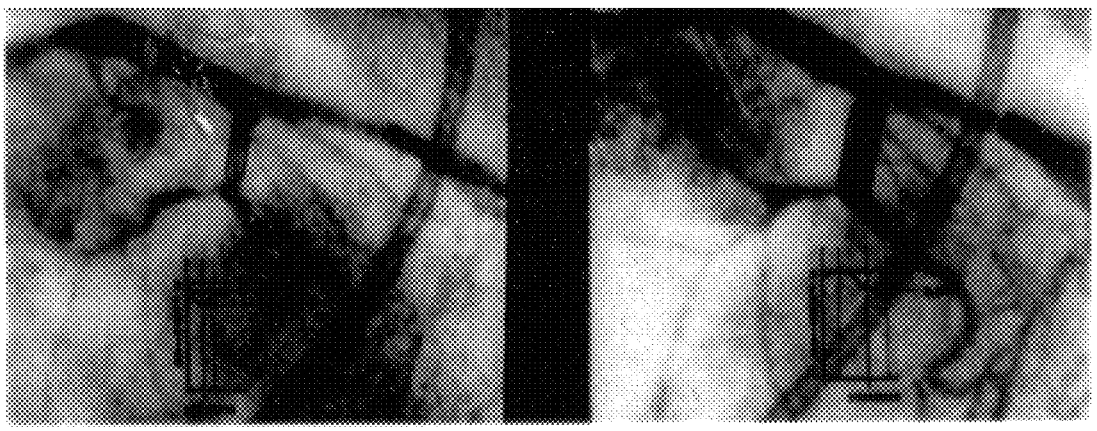
FIG. 1 is an angiograph showing the improvement in one patient after intracoronary application of CGRP.

CGRP is a 37-amino acid neuropeptide which is the most potent naturally occurring vasodilator peptide in the human body. CGRP is distributed throughout the central and peripheral nervous systems, and is found in areas that are known to be involved in cardiovascular function. Peripherally, CGRP is found in the heart, particularly in association with the sinoatrial and atrioventricular nodes. In addition, CGRP is found in nerve fibers that form a dense periadventitial network throughout the peripheral vascular system, including the cerebral, coronary, and renal arteries. CGRP has prominent cardiovascular effects, including vasodilation and positive chronotropic and inotropic effects, which may play an important role in normal cardiovascular function.

CGRP occurs in two known forms in the human body—an α- and a β- form. The α- form is shown in SEQ ID NO. 1 and the β- form is shown in SEQ ID NO. 2. The α- and β- strains of CGRP both are present in plasma, cerebrospinal fluid, and the spinal cord. Wimalawansa, S. J., Morris, H. R., MacIntyre, I. J. Mol. Endocrinol., 3:247 (1989). Both forms have been isolated and fully characterized by amino acid sequencing and fast atom bombardment-mass spectrometry (FABMS). Wimalawansa, S. J., Morris, H. R., Etienne, A., Blench, I., Panico, M., and MacIntyre, I. Isolation, purification and characterization of β-hCGRP from human spinal cord, Biochem. Biophys. Res. Commun., 167, 993 (1990); Steenberg, et al. FEBS Letts. 183:403 (1985); incorporated herein by reference. Genes for CGRP have been identified on chromosome 11. Hoopener, et al. Hum. Gen. 70:259 (1985). CGRP receptors have been isolated and purified, and monoclonal antibodies have been raised against these purified receptors. Wimalawansa, S. J. Isolation and characterization of calcitonin gene-related peptide receptors and raising monoclonal antibodies. Wimalawansa, S. J. Annals of New York Academy of Sciences, Vol. 657:70–87 (1992); Wimalawansa, S. J., Gunasekera, R. D., Zhang, F. Isolation, purification, and characterization of calcitonin gene-related peptide receptor. Peptides 14:691–699 (1993); Proceedings, First International Symposium on Calcitonin Gene-Related Peptide. Graz., Austria, Regul. Peptides. 14, 691. (1993); and Wimalawansa, S. J. Calcitonin gene-related peptide, calcitonin and amylin: a peptide super family. Crit. Rev. Neurobiol. (in press), incorporated herein by reference.

The preferred form of CGRP for use in the present invention is CGRP that is synthesized using an automatic peptide synthesizer using well known methods. The amino acid sequence of CGRP is known, and the α- and β- forms are represented in SEQ. ID NOS. 1 and 2, respectively. The α- and β- forms of CGRP represented in SEQ. ID NOS. 1 or 2 differ in structure by only three amino acids, and each possesses equal biological activity in the cardiovascular system.

A preferred method for synthesizing the CGRP is the well known Merrifield method. Merrifield, R. B. J. Am. Chem. Soc. 85:2149 (1963); Merrifield, R. B. Science, 232:341 (1986), both incorporated herein by reference. See also Wimalawansa, S. J. Use of synthetic peptides in specific affinity chromatography for purification of specific peptide receptors. Innovation and Perspectives in solid Phase synthesis (Peptides, Polypeptides and Oligonucleotides), (Ed.) R. Epton, Intercept Ltd., Andover, UK (1991) 111–119, incorporated herein by reference. Either t-Boc, F-Moc, or fast-Moc solid-phase peptide chemistry may be used to synthesize the peptide.

Once synthesized, the authenticity of the resulting peptide may be verified using known procedures, such as fast atom bombardment mass spectroscopy, amino acid sequencing and analysis. After synthesis, the peptide preferably should be filter sterilized (0.2 μm), aliquoted, lyophilized, and stored in sterile ampoules or in catheters. Just prior to application, the lyophilized powder should be dissolved in sterile normal saline (0.9% NaCl in water).

Human CGRP also may be obtained commercially, e.g. from: Peninsula Laboratory, located in Belmont, Calif.; Bachem Biosciences, Inc., located in King of Prussia, Pa.; and, Sigma Chemicals, located in St. Louis, Mo.. Commercial grade human CGRP is not marketed for human use; therefore, commercially available human CGRP's may be used in the present invention only if they are purified and sterilized so that they are fit for human use. CGRP can be delivered to the target artery as a liposomal form. Genetically engineered human CGRP also may be used in the present invention. Similar results also could be achieved using a CGRP analogue or an analogue based on the CGRP "receptor structure." These include peptide-based analogues, as well as peptide-mimetic analogues. Animal-derived CGRP's are biologically active and thus could be used in the present invention; however, as a practical matter, animal-derived CGRP's present allergy and autoimmune problems which preferably should be avoided.

The route of administration of the CGRP will vary depending upon the contemplated application. For specialized vascular beds, such as the coronary, carotid, or renal arteries, the CGRP preferably should be administered by selected intraarterial application. The dose of CGRP preferably should be between about 0.25 and 1 nmol administered as a bolus dose or as an infusion of 2–10 pmol/kg/minute. The CGRP may be in either free or liposomal form. To get the maximum benefit, the CGRP should be administered via a catheter directly into the artery of interest. The dose preferably should be pre-loaded into a catheter suitable for insertion into the target artery for local administration of the dose. However, in order to make the CGRP as economical as possible, variable doses also may be used, preferably via a second channel in the catheter. Also, some patients may benefit from local infusion of CGRP after administration of the initial bolus dose, preferably via the same catheter. In certain patients, CGRP can be delivered directly onto the arterial wall (i.e., at the site of narrowing or spasm) through a "leaky catheter" after balloon inflation or by a coronary stent impregnated with CGRP.

In a preferred embodiment, the CGRP is introduced during angioplasty, through the angioplasty catheter, itself. Most of the available balloon catheters have two passageways or lumens. A first passageway is used to inflate and deflate the balloon with a hydraulic system. A second passageway is used to pass the guidewire through the catheter. Typically, this second passageway is large enough to maintain a channel around the guidewire to permit monitoring of the vascular pressure at the distal tip of the catheter or to permit monitoring of the vascular anatomy by radiographic dye injection. The channel also can be used to transport drugs through the catheter for application to the artery distal to the catheter. A preferred embodiment involves the administration of CGRP through an angioplasty catheter, preferably the CORFLO™ perfusion catheter available from Leocor, Inc., Houston, Tex.

Where the use of a catheter is contraindicated, or where the use of a catheter would involve a significant delay for some technical reason, e.g., more than 30 minutes or so, the CGRP may be administered as an intravenous infusion at 0.1 to 0.5 nmol/kg/hr.

Where the goal is to prevent the reocclusion of arteries after angioplasty (e.g., balloon angioplasty, mechanical dilatation, application of rotorouter, etc.) or vascular grafts in any vascular bed (e.g., coronary, renal, carotid, femoral, etc.), a similar dose should be administered. Preferably, 0.25 to 1 nmol of free or liposomal CGRP should be pre-loaded into a catheter and administered directly to the target artery as a bolus dose. Alternately, 2 to 10 pmol/kg/minute of the CGRP may be infused locally into the target artery through the catheter. In order to make the product as economical as possible, the catheter should be adapted for infusion of a second dose or infusions locally to the target artery. In some cases, it may be beneficial for the local infusion of CGRP to last for a longer period of time after the initial bolus dose. Also, following an angioplasty procedure, a low dose intravenous infusion of 50–200 pmol/kg/hr of CGRP is recommended, provided that the blood pressure is satisfactorily maintained.

Where the CGRP is used to prevent reocclusion of vessels following arterial or venous grafts, the CGRP preferably should be infused into a peripheral vein at a dose of about 50–200 pmol/kg/hr for several hours, preferably for at least about 8–24 hours, as in the case of administration of intravenous heparin or nitrates. For this particular use, local infusion via a catheter may not be required.

Selective arterial infusion or injection of a localized bolus dose of CGRP (e.g., intracoronary, or intracarotid) causes a localized vasodilation of the arterial bed concerned. However, intravenous infusion of CGRP causes a preferential increase of blood flow to the heart, kidney, brain, and skin in the upper half of the body, respectively. Where clotting is a concern, the beneficial effects of CGRP may be enhanced by co-administering the CGRP with an anti-platelet drug, such as prostaglandin $E_1$, aspirin, ticlopidine, dipiridamol, an aspirin-like compound, or a thrombolytic agent (clot buster) such as recombinant tissue plasminogen activator (rTPA) or streptokinase. CGRP, itself, does not have an anti-platelet effect.

Where CGRP is used to treat impotence, topical application directly on the penis in the form of a cream is preferred. Any pharmaceutically acceptable preparation may be used, in particular a preferred cream being Aquaphore, which is commercially available from Beiersdorf Inc., Norwalk, Conn. The concentration of CGRP in the cream should range from about 1–3 nmol, and in one preferred embodiment be about 2.5 nmol/ml. In a preferred embodiment, the CGRP is conjugated to linolenic acid—a naturally occurring polyunsaturated fatty acid—as an ester. (Acetoxymethyl acetate or acetoxymethyl esters can also be used for this purpose instead of linolenic acid.) This CGRP ester (conjugate) may be prepared using an automated peptide synthesizer and known methods. Alternately, the CGRP ester may be prepared by reacting the CGRP and linolenic acid using carbodiimide, glutaraldehyde, or a similar compounds, as a coupling agent.

In the case of conjugation of CGRP to a fatty acid manually, a 1:1 weight ratio of CGRP should be allowed to react with citraconic anhydride at a pH of 8.5 (to block free amine groups) while mixing with a magnetic stir bar. After 60 minutes at room temperature, the blocked peptide should be separated from other free compounds by a G10 gel-permeation column. The blocked peptide then should be allowed to react with the same weight of coupling reagent and the pH should be adjusted to 8.0. The mixture should be incubated for 10 minutes and an equal volume of fatty acid—preferably linolenic acid, $C_{18}H_{30}O_2$ (FE 278.4). In molar proportions, about 50 mol of fatty acid should be added for every 1 mol of peptide. After four hours at room temperature, 100 mmol/L of sodium acetate (pH 4.2) should be added to terminate the reaction. The resultant material should be dialyzed to remove the sodium acetate with 5 changes of buffer. The material then should be dialyzed overnight against phosphate buffered saline (pH 7.4) to remove all uncoupled reagents. This last dialysis step (i.e., separation of the conjugated compound) also may be achieved by gel-permeation chromatography.

Once the CGRP ester is formed, the CGRP ester should be mixed with a pharmaceutically acceptable base cream to result in a concentration of 2.5 nmol/ml. A preferred cream is a lipophilic base such as Aquaphore. After topical application of about 0.5–1 ml of the CGRP cream and gentle rubbing, the "fatty acid-CGRP ester" will readily penetrate through the skin and accumulate in the penile corpora. Naturally occurring esterases in the subcutaneous tissues will then release active CGRP into the local environment from the fatty acid conjugate. The result is rapid and sustained vasodilation of the blood vessels responsible for penile erection. The effect of the CGRP should last between about 10–15 minutes. The local application may be repeated, if necessary, to result in another sustained erection lasting about 10–15 minutes. Persons of skill in the art can adjust the foregoing parameters to locally apply CGRP to other sites in the body.

Studies conducted in rats and dogs following infusion of CGRP together with free radical scavengers reveal a marked decrease in post-reperfusion injury in all major organ studies, including heart, brain, and kidney. These two agents act synergistically to prevent ischemic damage, particularly reperfusion injury that tends to follow a period of ischemia in these vital organs.

Injection of a bolus dose (or an infusion) of CGRP into the coronary arteries of humans to relieve ischemia associated with coronary artery narrowing (permanent) or spasms (temporary narrowing) has relieved cardiac pain and reversed electrocardiographic changes associated with ischemia. Preliminary studies with miniature doplers confirmed a significant increase of blood flow in the coronary arteries after infusion of CGRP.

In addition, in dog and pig models, administration of intracoronary CGRP completely abolished coronary spasms and re-established the coronary artery blood flow in coronary artery spasms induced by chemicals (e.g., neuropeptide Y or ergonovine), or by the guidewire of the coronary catheter.

CGRP also has been infused intravenously into rats that have been prepped to experimentally simulate acute renal failure using known procedures. The studies demonstrated that the administration of CGRP induced a 3 fold increase of urine output and a 3 fold increase of the glomerular filtration rate. Both of these results are extremely favorable to recovery from acute renal failure. Similar results have been observed with reperfusion injury affecting the heart and brain.

The invention will be further understood with reference to the following examples:

EXAMPLE 1

CGRP having SEQ ID NO. 1 was synthesized according to the Merrifield method of t-Boc solid-phase peptide chemistry. An Applied Biosystem automated peptide synthesizer was used for the synthesis, and amino acids were obtained from Applied Biosystem, Foster City, Calif. The resulting peptide was characterized by fast atom bombardment mass spectrometry, amino acid analysis, and sequencing.

EXAMPLE 2

Six humans with angina pectoris secondary to narrowing of the coronary arteries were selected for this procedure. In preparation for angioplasty, 0.5 nmol of CGRP synthesized as described in Example 1 was dissolved in sterile normal saline to form a 0.004% solution of CGRP. The solution was loaded into a angiographic catheter by a microbore syringe.

Prior to application of CGRP, the coronary arteries of these patients exhibited 40–90% blockage in one or more of the coronary arteries. After the CGRP was injected as a bolus dose, the change in diameter of the coronary artery was measured by angiography immediately and 5–10 minutes after the injection. The diameter of the coronary artery clearly increased after injection of CGRP. The improvement of the coronary artery diameter ranged between 30–80%, as measured by angiography. FIG. 1 is a representative angiograph showing the improvement in one patient who underwent the procedure.

In patients who were suffering from angina pain at the time of the procedure (4 out of 6 patients), the pain immediately subsided after the intracoronary injection of CGRP. This result was consistent with angiographic evidence of widening of the coronary artery diameter and with the reestablishment of coronary blood flow, and changes in the electrocardiograms.

Injection of a similar volume of normal saline (carrier) did not change the size of the coronary arteries. Angioplasty and/or stent procedures were carried out in all 6 patients, as previously planned, with excellent results.

EXAMPLE 3

Four beagles were used in this procedure. The dogs were anesthetized using telazol, xylazine, and butrophanol, and coronary catheterization was performed. After basal angiography, coronary spasms were induced by intracoronary administration of a combination of neuropeptide Y (2.5 nmol) and ergonovine (50 $\mu$g). Normal saline (for control animals) and normal saline containing 0.25 nmol of CGRP prepared as in Example 1 were administered into coronary arteries through the catheter. The saline or saline/CGRP solution was injected into the coronary artery as a bolus dose. The change in diameter of the coronary artery was measured by digital angiography and miniature doplar probes. Results showed a 50% increase in the diameter of the coronary arteries after intracoronary administration of CGRP.

EXAMPLE 4

Four mini pigs were anesthetized using Ketamine and xylazine, and maintained on isoflurane during coronary catheterization. After basal angiography, coronary spasms were induced by intracoronary administration of a combination of neuropeptide Y (2.5 nmol) and ergovine (50 μg). Normal saline (for control animals) and normal saline containing 0.50 nmol of CGRP prepared as in Example 1 were administered into coronary arteries through the catheter. The saline or saline/CGRP solution was injected into the coronary artery as a bolus dose. The change in diameter of the coronary artery was measured by digital angiography and miniature doplar probes. Results showed a 40%–50% increase in the diameter of the coronary arteries after intracoronary administration of CGRP.

EXAMPLE 5

Figure 2A:
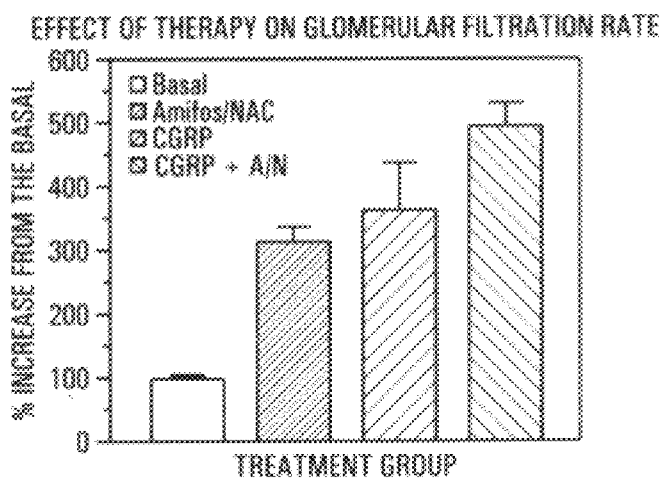
FIGS. 2A and 2B respectively show the beneficial effects of CGRP on glomerular filtration and urine output following induction of acute renal failure in six pairs of rats.
Figure 2B:
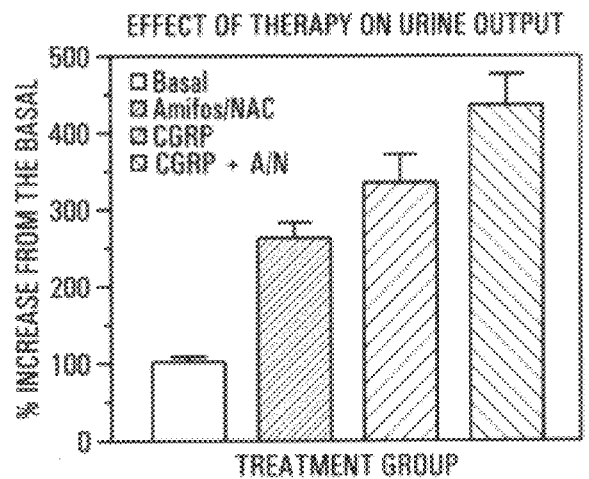

Pairs of 6 rats were induced to exhibit acute renal failure by clamping the renal arteries for 50 minutes using known procedures. One in each pair of rats was used as a test animal and one as a control. The induced rats were intravenously injected with normal saline (5 ml/hr) either (1) alone, as a control, or (2) containing the following: 0.8 nmol/kg/hr of CGRP prepared as in Example 1; 0.6 mmol/kg/hr of a free radical scavenger—either N-acetyl cysteine, obtained from Faulding Hospital Products, Inc., N.J., or amifostine (ethiofos, WR2721), 0.2 mmol/kg/hr, obtained from U.S. Bioscience, Inc., PA. The content of the injection, and the observed change in urine output are given in FIGS. 2A and 2B.

These results demonstrate a 3-fold increase in urine output, and a 3-fold increase in glomerular filtration rate in the rats that received the CGRP. The combined therapy of CGRP and a free radical scavenger further increased the glomerular filtration rate and the urine output to 4–5 fold. Maintenance of satisfactory urine output and glomerular filtration are extremely important to recovery from acute renal failure.

EXAMPLE 6

10 mg of CGRP synthesized as in Example 1 was dissolved in 1 ml of distilled water and mixed with 10 mg of citraconic anhydride at a pH of 8.5 (to block free amine groups) while mixing with a magnetic stir bar. After 60 minutes at room temperature, the blocked peptide was separated from other free compounds by a G10 gel-permeation column. The blocked peptide was allowed to react with 10 mg of carbodiimide as a coupling reagent, and the pH was adjusted to 8.0. The mixture was incubated for 4 hours with 50 mg of linolenic acid, $C_{18}H_{30}O_2$ (M. Wt. 278.4). 10 ml of 100 mmol/L sodium acetate (pH 4.2) was added to terminate the reaction. The resulting mixture was dialyzed against sodium acetate (pH 4.2) with 5 changes of buffer. The material then was dialyzed overnight against phosphate buffered saline (pH 7.4) to remove all other uncoupled reagents.

EXAMPLE 7

The CGRP ester prepared in Example 6 was mixed with Aquaphore cream to result in a concentration of 2.5 nmol/ml. About 0.5 to 1 ml of the CGRP cream was applied on the ventral surface of the base of the penis with gentle rubbing. The result was rapid and sustained erection lasting for 10–15 minutes. This local application of CGRP containing cream can be repeated to result in another sustained erection.

Persons of skill in the art will appreciate that many modifications may be made to the embodiments described herein without departing from the spirit of the present invention. Accordingly, the embodiments described herein are illustrative only and are not intended to limit the scope of the present invention.

I claim:

1. A method for counteracting pathological vasospasms or ischemia in target arteries of a mammal where the target arteries comprise a specialized vascular bed selected from the group consisting of coronary, carotid, and renal arteries, the method comprising administering a pharmaceutically acceptable preparation of a compound selected from the group consisting of calcitonin gene-related peptide (CGRP) and analogues of CGRP which bind to the CGRP receptor to said mammal in an amount effective to counteract said pathological vasospasm or ischemia, where the vasospasms or ischemia are due to a cause selected from the group consisting of angioplasty, vascular graft, stent insertion, and arterial surgery.

2. The method of claim 1 wherein said calcitonin gene-related peptide is selected from the group consisting of α- and β- human calcitonin gene related peptide.

3. The method of claim 2 wherein said CGRP is administered locally to said target arteries through a catheter.

4. The method of claim 2 wherein said target arteries comprise a specialized vascular bed and said calcitonin gene-related peptide is administered in a bolus dose of about between 0.25–1 nmol.

5. The method of claim 3 wherein said target arteries comprise a specialized vascular bed and said calcitonin gene-related peptide is administered in a bolus dose of between about 0.25–1 nmol.

6. The method of claim 4 wherein said pharmaceutically acceptable preparation further comprises a free radical scavenger.

7. The method of claim 5 wherein said pharmaceutically acceptable preparation further comprises a free radical scavenger.

8. The method of claim 6 wherein said free radical scavenger is selected from the group consisting of n-acetyl cysteine and amifostine.

9. The method of claim 7 wherein said free radical scavenger is selected from the group consisting of n-acetyl cysteine and amifostine.

10. The method of claim 2 wherein said peptide is administered in conjunction with a compound selected from the group consisting of an antiplatelet agent and a thrombolytic agent.

11. The method of claim 3 wherein said peptide is administered in conjunction with a compound selected from the group consisting of an antiplatelet agent and a thrombolytic agent.

12. The method of claim 4 wherein said peptide is administered in conjunction with a compound selected from the group consisting of an antiplatelet agent and a thrombolytic agent.

13. The method of claim 6 wherein said peptide is administered in conjunction with a compound selected from the group consisting of an antiplatelet agent and a thrombolytic agent.

14. A method for counteracting vasospasms in a specialized vascular bed, ischemia, or renal failure in a mammal comprising intravenously infusing between about 2–10 pmol/kg/min of a pharmaceutically acceptable preparation of calcitonin gene-related peptide in an amount effective to counteract said vasospasms, ischemia, or renal failure, where the vasospasms or ischemia are due to a cause selected from the group consisting of angioplasty, vascular graft, stent insertion, and arterial surgery.

15. The method of claim 14 wherein said calcitonin gene-related peptide is selected from the group consisting of α- and β- human calcitonin gene-related peptide.

16. A method for counteracting
pathological vasospasms,
organ ischemia due to a degree of narrowing or an obstruction, or
renal failure
of a mammal comprising administering a pharmaceutically acceptable preparation of calcitonin gene-related peptide to an artery by a method selected from the group consisting of
through a catheter in a bolus dose of between about 0.25–1 nmol and in an infusion of 2 to 10 pmol/kg/minute, and
intravenously in an infusion of 50 to 500 pmol/kg/ hr,
wherein said calcitonin gene-related peptide is selected from the group consisting of α- and β-human calcitonin gene-related peptide, (CGRP), and analogues of α- and β-CGRP which bind to the CGRP receptor, and
wherein the vasospasms or ischemia are due to a cause selected from the group consisting of angioplasty, vascular graft, stent insertion, and arterial surgery.

17. A method for counteracting male impotence comprising applying topically to the penis of a mammal a pharmaceutically acceptable preparation of between about 1–3 nmol of a compound selected from the group consisting of calcitonin gene-related peptide (CGRP) and analogues of CGRP which bind to the CGRP receptor which compound has been chemically bound to a naturally occurring polyunsaturated fatty acid to make it hydrophobic and skin-penetrable.

18. The method of claim 17 wherein said calcitonin gene-related peptide is selected from the group consisting of α- and β- human calcitonin gene-related peptide.

19. The method of claim 18 wherein said pharmaceutically acceptable preparation comprises a lipophilic base cream.

20. A method for counteracting vasospasms in target arteries comprising a specialized vascular bed of renal arteries of a mammal comprising administering a pharmaceutically acceptable preparation of calcitonin gene-related peptide selected from the group consisting of α- and β- human calcitonin gene-related peptide, to said mammal in a bolus dose of about between 0.25–1 nmol effective to counteract said vasospasm, said pharmaceutically acceptable preparation further comprising a free radical scavenger.

21. The method of claim 20 wherein said free radical scavenger is selected from the group consisting of n-acetyl cysteine and amifostine.

22. A method for counteracting vasospasms in target arteries comprising a specialized vascular bed of a mammal comprising administering a pharmaceutically acceptable preparation of calcitonin gene-related peptide to said mammal in a bolus dose of about between 0.25–1 nmol effective to counteract said vasospasm, where said vasospasm comprises occlusion or reocclusion of arteries.

23. A method for counteracting vasospasms in target arteries comprising a specialized vascular bed of a mammal comprising administering a pharmaceutically acceptable preparation of calcitonin gene-related peptide (CGRP) selected from the group consisting of α- and β- human CGRP, to said mammal in a bolus dose of between about 0.25–1 nmol to counteract said vasospasm, wherein said CGRP is administered locally to said target arteries through a catheter, and wherein said vasospasms comprise occlusion or reocclusion of arteries in a specialized vascular bed, or in acute renal failure.

24. A method for counteracting vasospasms in target arteries of a mammal comprising administering a pharmaceutically acceptable preparation of calcitonin gene-related peptide (CGRP) selected from the group consisting of α- and β- human CGRP, to said mammal in an amount effective to counteract said vasospasm, wherein
said vasospasms comprise occlusion or reocclusion of arteries in a specialized vascular bed, or in acute renal failure;
said CGRP is administered by venous infusion; and
said amount of said CGRP comprises a dose of about 50–200 pmol/kg/hr.

25. The method of claim 24 wherein said specialized vascular bed is selected from the group consisting of coronary, carotid, and renal arteries.

26. A method for counteracting male impotence comprising applying topically to the penis of a mammal a pharmaceutically acceptable cream of between about 1–3 nmol of calcitonin gene-related peptide (CGRP) conjugated to linolenic acid.

27. The method of claim 26 wherein said CGRP is selected from the group consisting of α- and β- human CGRP.

28. The method of claim 27 wherein said pharmaceutically acceptable cream comprises a lipophilic base cream.

* * * * *

SEQUENCE LISTING

```
(1) GENERAL INFORMATION:

(iii) NUMBER OF SEQUENCES:  2

(2) INFORMATION FOR SEQ ID NO:  1:

(i) SEQUENCE CHARACTERISTICS:
       (A) LENGTH:  37 amino acids
       (B) TYPE:  amino acid
       (C) STRANDEDNESS: Not Relevant
       (D) TOPOLOGY:  linear (ii) MOLECULE TYPE:  peptide (v) FRAGMENT TYPE:

(x) PUBLICATION INFORMATION:
       (A) AUTHORS:  Morris, Howard R.
           Panico, Maria
           Etienne, Tony
           Tippins, John
           Girgis, Samia I.
           MacIntyre, Iain
       (B) TITLE:  Isolation and characterization of human
           calcitonin gene-related peptide
       (C) JOURNAL:  Nature
       (D) VOLUME:  308
       (E) ISSUE:  19
       (F) PAGES:  746-748
       (G) DATE:  April 19, 1984
```

-continued

```
        (xi) SEQUENCE DESCRIPTION: SEQ ID NO: 1:

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
                20                  25                  30

Gly Ser Lys Ala Phe
            35

(2) INFORMATION FOR SEQ ID NO: 2:

(i) SEQUENCE CHARACTERISTICS:
         (A) LENGTH: 37 amino acids
         (B) TYPE: amino acid
         (C) STRANDEDNESS: Not Relevant
         (D) TOPOLOGY: linear (ii) MOLECULE TYPE: peptide (v) FRAGMENT TYPE:

(x) PUBLICATION INFORMATION:
         (A) AUTHORS: Wimalawansa, Sunil J.
         (B) TITLE: Calcitonin: Molecular Biology, Physiology,
              Pathophysiology and Its Therapeutic Uses
         (C) JOURNAL: Advances in Bone Regulatory Factors:
              Morphology, Biochemistry, Physiology and Pharmacology
              (book)
         (D) VOLUME: n/a
         (E) ISSUE: n/a
         (F) PAGES: 121-160
         (G) DATE: 1989

(xi) SEQUENCE DESCRIPTION: SEQ ID NO: 2:

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
                20                  25                  30

Gly Ser Lys Ala Phe
            35
```